US011090290B2

(12) United States Patent
Vasseur-Demarcy et al.

(10) Patent No.: US 11,090,290 B2
(45) Date of Patent: Aug. 17, 2021

(54) CLONIDINE AND/OR CLONIDINE DERIVATIVES FOR USE IN THE PREVENTION OF SKIN INJURY RESULTING FROM RADIOTHERAPY

(71) Applicant: MONOPAR THERAPEUTICS INC., Northbrook, IL (US)

(72) Inventors: Bérangère Vasseur-Demarcy, Deuill la Barre (FR); Pierre Attali, Vincennes (FR)

(73) Assignee: MONOPAR THERAPEUTICS, INC., Wilmette, IL (US)

( * ) Notice: Subject to any disclaimer, the term of this patent is extended or adjusted under 35 U.S.C. 154(b) by 0 days.

(21) Appl. No.: 15/573,503

(22) PCT Filed: May 10, 2016

(86) PCT No.: PCT/EP2016/060466
§ 371 (c)(1),
(2) Date: Nov. 13, 2017

(87) PCT Pub. No.: WO2016/180834
PCT Pub. Date: Nov. 17, 2016

(65) Prior Publication Data
US 2018/0098967 A1 Apr. 12, 2018

(30) Foreign Application Priority Data
May 13, 2015 (EP) ..................................... 15305728

(51) Int. Cl.
*A61K 31/4168* (2006.01)
*A61K 9/00* (2006.01)
*A61K 9/20* (2006.01)
*A61K 45/06* (2006.01)
*C07C 25/08* (2006.01)

(52) U.S. Cl.
CPC .......... *A61K 31/4168* (2013.01); *A61K 9/006* (2013.01); *A61K 9/205* (2013.01); *A61K 9/2063* (2013.01); *A61K 45/06* (2013.01); *C07C 25/08* (2013.01); *A61K 2300/00* (2013.01)

(58) Field of Classification Search
CPC ..... A61K 31/4168; A61K 9/006; C07C 25/08
See application file for complete search history.

(56) References Cited

U.S. PATENT DOCUMENTS

| | | | | |
|---|---|---|---|---|
| 5,288,498 A | * | 2/1994 | Stanley | A23G 3/368 424/434 |
| 2002/0156023 A1 | * | 10/2002 | Walling | A61K 31/519 514/27 |
| 2004/0101582 A1 | | 5/2004 | Wolicki | |
| 2009/0170876 A1 | * | 7/2009 | Qasem | A61K 31/4965 514/255.06 |
| 2010/0178328 A1 | * | 7/2010 | Martell | A61K 9/0019 424/450 |
| 2011/0288140 A1 | * | 11/2011 | Attali | A61K 9/2095 514/401 |

FOREIGN PATENT DOCUMENTS

| | | | |
|---|---|---|---|
| EP | 0542824 A1 | | 5/1993 |
| EP | 1972332 A1 | | 9/2008 |
| EP | 2165706 A1 | | 3/2010 |
| EP | 2368549 | * | 9/2011 |
| EP | 2368549 A1 | | 9/2011 |
| JP | 2012-502952 A | | 2/2012 |
| WO | WO-2007/017571 A1 | | 2/2007 |
| WO | WO-2010/031819 A1 | | 3/2010 |
| WO | WO-2013/010032 A1 | | 1/2013 |
| WO | WO-2014/018571 A2 | | 1/2014 |

OTHER PUBLICATIONS

Singh et. al. (Am. J. Clin. Dermatol. (2016) 17:277-292). (Year: 2016).*
Chen et al., Positional differences in the wound transcriptome of skin and oral mucosa, BMC Genomics, 11:471 (2010).
International Search Report and Written Opinion, International Application No. PCT/EP2016/060466, dated Aug. 19, 2016.
Le et al., Palifermin Reduces Severe Mucositis in Definitive Chemoradiotherapy of Locally Advanced Head and Neck Cancer: A Randomized, Placebo-Controlled Study, J. Clin. Oncol., 29(20):2808-14 (2011).

* cited by examiner

*Primary Examiner* — Marcos L Sznaidman
(74) *Attorney, Agent, or Firm* — Marshall, Gerstein & Borun LLP

(57) ABSTRACT

The present invention pertains to a pharmaceutical composition comprising a pharmaceutically acceptable carrier and Clonidine and/or Clonidine derivatives as a sole active ingredient for use in the prevention of skin injury resulting from radiotherapy by transmucocal administration.

8 Claims, No Drawings

CLONIDINE AND/OR CLONIDINE DERIVATIVES FOR USE IN THE PREVENTION OF SKIN INJURY RESULTING FROM RADIOTHERAPY

CROSS REFERENCE TO RELATED APPLICATIONS

This application is a National Stage Application of International Patent Application No. PCT/EP2016/060466, filed May 10, 2016, which claims the priority benefit from European Patent Application No. 15305728.6, filed May 13, 2015, which is incorporated by reference in its entirety.

FIELD OF THE INVENTION

The present invention pertains to the prevention of skin injury resulting from radiotherapy.

BACKGROUND OF THE INVENTION

Over the past several decades, radiation therapy, also called radiotherapy, has contributed to a significant reduction in cancer mortality. Radiation therapy is used in the treatment of as many as 50% of all cancer patients. While the use of radiation therapy is an effective way to treat many kinds of cancer, there are some complications that may result. Radiation therapy, which achieves most of its cell killing properties by generating oxygen radicals within cells, can also efficiently damage the DNA of non cancerous cells and affect the growth of these normal cells, particularly mitotically active normal cells.

Common complications of radiotherapy include adverse effects on the patient's skin (also called skin injury). The symptoms of skin injury usually comprise at least one adverse side effect of radiotherapy selected from: radiodermatitis, erythema, pruritus, moist or dry desquamation, skin hyperpigmentation, depilation, ulceration and necrosis. As far as skin is concerned, it has been found that keratinocytes irradiation negatively affects skin regeneration by altering the balance between the repopulation of basal cell layer and the rate of cell destruction by treatment. This can result in acute radiodermatitis, especially in skin folds or in thinner areas of skin, which starts during the days or weeks following irradiation. Radiodermatitis can be characterized by an erythema (Grade 1), usually associated with dry desquamation and possibly with edema and exsudation (Grade 2). In the most severe cases (Grade 3), confluent moist desquamation and ulcerations may be observed, or even necrosis (Grade 4). These complications may further result in skin hyperpigmentation or dyschromia. Acute radiodermatitis may be favored by concomitant chemotherapy, particularly with cisplatin which is a radiosensitiser. Among skin complications of radiotherapy, mention can also be made of chronic radiodermatitis, which usually appears at least six months or even several years after irradiation. It reflects in fibrosis, the severity of which is linked to the total irradiation dose and the fractionation thereof, with mostly skin atrophy and xerosis. All these skin complications should be distinguished from burn injuries, in view of the differences in the time to reaction, the fact that epidermal cells only are affected, and the sequence of damage, which involves the migration of basal cells upwards to the surface of skin.

Almost all patients exposed to ionizing electron beam irradiation, and especially to high doses of lower beam energy, are at risk of developing skin reactions. It is estimated that approximately 85-87% of the patients receiving external beam radiotherapy will experience a moderate to severe skin reaction, of which 10 to 15% will progress to moist desquamation. These skin complications can in extreme cases be so difficult to endure that it is not uncommon for people to forego or discontinue recommended cancer therapy treatments.

To date, no efficient prophylactic treatment has been provided so as to reduce the severity or occurrence of the above complications. Patients are only suggested to avoid applying perfumes or deodorants onto the areas that shall be treated, and to apply moisturizing aqueous creams after irradiation.

Moreover, radiotherapy also frequently affects hair follicles, which irradiation (at more than 20 Gy) typically results in a loss of hair shafts after one or two weeks of treatment. Hair generally grows back after treatment stops, although regrowth is slower and occurs later than in case of chemotherapy. However, hair loss may be irreversible if the radiation dose exceeds 45 Gy. It should be noted that this phenomenon affects not only hair but also other skin appendages such as nails.

Among the treatments contemplated in the literature, it has been suggested to use clonidine in order to alleviate one or more skin lesions caused or worsened by radiotherapy, such as hand-foot syndrome (EP 2 368 549) or radiodermitis (WO 2013/010032). These treatments are applied topically onto the wounded areas, which is not convenient in the case of extensive wound areas. The same holds true for US 2004/101582 which provides a composition for treating skin lesions due to chemotherapy. An oral administration of clonidine to treat radiotherapy-induced ulcers has been proposed in WO 2014/018571. However, as in US'582, clonidine is combined with other active agents, such that it is not possible to infer any therapeutic effect of clonidine itself.

Applicant has also described for the first time that Clonidine and/or Clonidine derivatives are efficient for treating mucositis, a specific adverse side effect of radiotherapy and chemotherapy based on alkylating agents (WO 2010/031819). Mucositis is an inflammatory disorder affecting oral or gastro-intestinal mucosa and a frequent complication of head and neck radiotherapy. Although Clonidine and/or Clonidine derivatives exert an anti-inflammatory effect on mucosa, it is known that epithelial cells from skin produce significantly higher amounts of pro-inflammatory cytokines than cells from oral mucosa, which account for site-specific differences in the inflammatory response to injury in mucosa compared with skin and in turn for the faster healing of mucosa (Li Chen et al., *BMC Genomics*, 2010, 11:471). It was thus not predictable that Clonidine and/or Clonidine derivatives could efficiently prevent the inflammatory component of skin injury resulting from radiotherapy.

Further, the only active agent currently marketed for the treatment of oral mucositis, i.e. palifermin, was shown not to improve radiation skin injury compared to a placebo, and even worsen skin adverse reactions, despite its anti-inflammatory effect (Quynh-Thu Le et al., *Journal of Clinical Oncology*, Vol. 29, No 20, Jul. 10, 2011).

SUMMARY OF THE INVENTION

Unexpectedly, the inventors have found that Clonidine and/or Clonidine derivatives are able not only to alleviate mucositis, but also to prevent skin injury resulting from radiotherapy, when Clonidine and/or Clonidine derivatives are administered via transmucosal route to patients in need thereof.

Thus, this invention is directed to a pharmaceutical composition comprising a pharmaceutically acceptable carrier and clonidine and/or clonidine derivatives selected from compounds of the following formula (I):

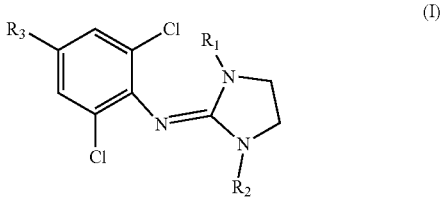

wherein:

$R_1$ and $R_2$ are independently selected from H and —OCOR, and $R_3$ is selected from H, —CH$_2$OH, —OCOR, —COOR, —NH$_2$, —NHR, —NRR' and —NHCOR, wherein R and R' independently designate a linear or branched alkyl group having from 1 to 6 carbon atoms, which may be substituted by one or more groups selected from a halogen atom, an amino group and an alkylamino group which alkyl part is a linear or branched alkyl having from 1 to 6 carbon atoms, and tautomer forms and pharmaceutically acceptable salts thereof, as a sole active ingredient, for use in the prevention of skin injury resulting from radiotherapy by transmucosal administration.

This invention is also directed to the use of a clonidine and/or clonidine derivative as mentioned above as a sole active ingredient for the manufacture of a pharmaceutical composition intended to prevent skin injury resulting from radiotherapy by transmucosal administration.

It also pertains to a method for preventing skin injury resulting from radiotherapy, comprising the step consisting of administering via transmucosal route, to a subject in need thereof, at least one clonidine and/or clonidine derivative as defined above, as a sole active ingredient, before or simultaneously with radiotherapy, thereby preventing said skin injury resulting from radiotherapy.

DETAILED DESCRIPTION

According to tis invention, a clonidine and/or clonidine derivative comprising compounds of formula (I) and tautomer forms and pharmaceutically acceptable salts thereof, are used in the prevention of skin injury resulting from radiotherapy. The symptoms of skin injury usually comprise at least one adverse side effect of radiotherapy selected from: radiodermatitis, erythema, pruritus, moist or dry desquamation, skin hyperpigmentation, depilation, ulceration and necrosis.

"Prevention" as used herein means that treatment is started prior to or simultaneously with radiation therapy, thus hindering the onset of skin injury.

"Radiation therapy or radiotherapy" as used herein means therapy using ionizing radiation, generally as part of cancer treatment to control or kill malignant cells. Radiation therapy or radiotherapy are often abbreviated RT, RTx, or XRT.

"Skin" as used herein means the soft outer layer covering mammals. It is made up of two main layers: the epidermis and the dermis. The outer layer of the skin (epidermis) is mostly made up of flat, scale-like cells called squamous cells. Skin thus does not include mucosa or mucous membrane.

"Mucosa or mucous membrane" as used herein means the lining of mostly endodermal origin. The mucosa lines some body cavities that are exposed to the external environment and some internal organs. They are at several places contiguous with skin: at the nostrils, the lips of the mouth, the eyelids, the ears, the genital area, and the anus. Mucosa is composed of non-keratinised stratified squamous epithelium.

Among compounds of formula (I), mention can be made, for instance, of those selected from the group consisting of: clonidine, p-aminoclonidine, p-diethylamino clonidine, p-ethylamino clonidine, p-acetamido clonidine, p-bromoacetamido clonidine, p-N-chloroethyl-N-methylamino clonidine, p-N-β-chloroethyl-N-methylaminomethyl clonidine, 3,5-dichloro-4-(imidazolidin-2-ylideneamino)benzyl alcohol, 3,5-dichloro-4-(1,3-diisobutyryl imidazolidin-2-ylideneamino)benzyl isobutyrate, ethyl 3,5-dichloro-4-(1-isobutyrylimidazolidin-2-ylideneamino)benzoate, and mixtures thereof.

An example of pharmaceutically acceptable salt of the compounds of formula (I) include their hydrochloride salt.

Clonidine ($R_1=R_2=R_3=$H in formula (I) above) and pharmaceutically acceptable salts thereof are particularly preferred. Clonidine hydrochloride is a pharmaceutically acceptable salt particularly preferred according to this invention.

As mentioned above, the Clonidine and/or Clonidine derivatives of this invention also encompass tautomer forms of the compounds of formula (I). For example, not intended as a limitation, tautomers are possible between the 4,5-dihydrooxazole and the adjacent nitrogen as shown below:

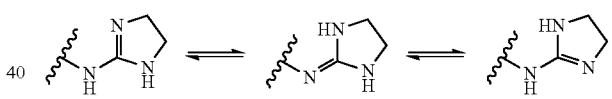

The Clonidine and/or Clonidine derivatives may be administered to a subject before or simultaneously with radiotherapy in order to prevent skin injury. They are typically used in a pharmaceutically effective amount, which means that they are administered in an amount sufficient to achieve at least partially the desired effect. In this regard, it has been shown that a daily oral intake of 20 to 150 µg, and preferably from 50 to 100 µg, of clonidine or of a clonidine derivative (expressed as base equivalent) efficiently reduces the risk of skin injury. This daily amount of clonidine or of a clonidine derivative may be administered in a single dose or in two divided doses, preferably in a single dose.

According to an embodiment of this invention, the composition comprising Clonidine and/or Clonidine derivatives may be administered on a daily basis to the patient, starting from 1 to 8 days, preferably from 1 to 3 days, before radiotherapy, until the end of radiotherapy and/or for a duration of from 6 to 10 weeks, for instance 8 weeks.

Besides Clonidine and/or Clonidine derivatives, the pharmaceutical composition comprises a pharmaceutically acceptable carrier. This carrier may be in a solid or liquid form, for instance. Solid carriers comprise powders, granules, capsules, tablets, films and the like. Liquid carriers may be water-based, oil-based or in the form of a water-in-oil or oil-in-water emulsion or dispersion, for instance.

According to this invention, the pharmaceutical composition containing Clonidine and/or Clonidine derivatives is administered transmucosally. The clonidine derivative may thus be formulated in a mucoadhesive buccal tablet, or included within microspheres or nanospheres, preferably the composition is in the form of a mucoadhesive tablet that can have any shape such as rectangular, circular, square, oval and the like.

Moreover, it is preferred that the composition of this invention provides sustained release of the Clonidine and/or Clonidine derivatives. The sustained release is for a period of at least 4 hours and preferably from 4 to 25 hours.

This mucoadhesive tablet comprises or consists essentially of (i.e. includes at least 90% by weight) at least one Clonidine and/or Clonidine derivative as the sole active ingredient, at least one diluent, at least one bioadhesive agent and preferably at least one sustained release agent and/or at least one binder.

The diluent used in the present invention can be insoluble or soluble. Examples of diluents include microcrystalline cellulose, silicified microcrystalline cellulose, hydroxypropyl methylcellulose, dibasic calcium phosphate, calcium carbonate, calcium sulfate, magnesium carbonate, mannitol, glucose, sorbitol, dextrose, lactose, starch and the like.

The diluent is usually present in an amount between 1 and 75% by weight, preferably between 10% to 60% by weight and more preferably from 20 to 40% by weight, based on the total weight of the mucoadhesive tablet.

The bioadhesive agent is usually a synthetic or a natural protein or a polysaccharide. The natural protein can be of vegetal or animal origin.

The proteins of vegetal origin that can be used are those described in EP 1 972 332. Examples of these proteins include natural pea proteins, natural wheat proteins and gliadin proteins and mixtures thereof. The method for producing pea proteins is described in, e.g., WO 2007/017571. The polysaccharide that can be used in the present invention includes chitosan, alginate, carboxymethyl cellulose, hydroxypropyl methyl cellulose, hydroxyethyl cellulose, hydroxypropyl cellulose, cyclodextrin, sodium hyaluronate and xanthan gum.

In another embodiment, the proteins of natural origin that can be used are those described in EP 0 542 824. A particular example is a milk protein concentrate titrating a minimum of 85% of proteins such as Prosobel L85, milk protein concentrate or, preferably, either Promilk 852A sold by Armor Proteins, or from the Alaplex range (4850, 1180, 1380 or 1395) sold by NZMP. The relative concentration of the milk natural proteins in the mucoadhesive tablet of the invention preferably ranges from 15% to 50% by weight, preferably from 20% to 30% by weight.

The binder can be selected from carboxyvinyl polymers, carmellose, methylcellulose, hydroxyethylcellulose, hydroxypropylcellulose, hydroxymethylcellulose, hydroxyethylmethyl cellulose, polyvinylpyrrolidone (povidone), polyvinyl alcohol, and the like. The binders may be present in the amount of 0.5 to 5% by weight, based on the total weight of the mucoadhesive tablet.

In the case where it is designed for sustained release of the clonidine derivative, the mucoadhesive tablet comprises a sustained release agent which may include hydrophilic polymers including polysaccharides such as cellulose based polymers such as hypromellose, cellulose acetate, cellulose esters, cellobiose or cellulose resins; a carboxyvinyl polymer such as Carbopol 934®; hydroxyethylmethacrylate; and mixtures thereof. Other polymers that can be used in the present invention include cellulose ethers, xanthan gum, scleroglucan, locust bean gum, gum Arabic, gum tragacanth, carob, alginic acid, alginates, carrageenanes, agar-agar, starch, and guar gum, either alone or in mixtures thereof.

The sustained release agents are generally present in a concentration of 5% to 80% by weight, preferably from 10% to 60% by weight and more preferably from 20 to 40% by weight, based on the total weight of the mucoadhesive tablet.

The mucoadhesive tablet may also comprise at least one additive selected from the group consisting of a glidant, a lubricant, a coloring agent, a flavouring agent, a wetting agent and mixtures thereof.

Flavoring agents include flavors, calcium citrate, Safrole, and sweetening agents such as aspartame, cyclamates, saccharin and xylitol. Additionally, glidants selected from talc and colloidal silicon dioxide, and lubricants including magnesium stearate, stearic acid and polyethylene glycol can also be added to the formulation of the mucoadhesive tablet. The wetting agent can be a water solution or a solvent such as an alcohol. These additional agents can be added to the carrier in the concentration range of 0.1 to 10% by weight, relative to the total weight of the mucoadhesive tablet.

According to a preferred embodiment of this invention, the pharmaceutical composition comprising clonidine and/or clonidine derivative as described above includes all the following excipients:
water as a wetting agent,
a diluent such as microcrystalline cellulose,
a binder such as polyvinylpyrrolidone (povidone),
a sustained release agent such as hydroxypropyl methylcellulose (hypromellose),
a milk protein concentrate,
a glidant such as colloidal silicon dioxide, and
a lubricant such as magnesium stearate.

The present invention also provides a method for preventing skin injury resulting from radiotherapy, comprising the step consisting of administering by the transmucosal route, to a subject in need thereof, at least one Clonidine and/or Clonidine derivative as defined above, as a sole active ingredient, before or simultaneously with radiotherapy.

In some cases, the subject is also administered chemotherapy, such as platinum-based chemotherapy (including cisplatin and carboplatin chemotherapy), preferably simultaneously with radiotherapy.

In the case where the pharmaceutical composition comprising the Clonidine and/or Clonidine derivative of this invention is applied as a mucoadhesive buccal tablet, the latter may be adhered to a gum and a slight pressure exerted thereon so as to maintain the same in place. The tablet is preferably applied after cleaning the teeth. A sustained release of clonidine derivative in the mouth may thus be attained.

EXAMPLES

This invention will be better understood in light of the following examples which are given for illustrative purposes only and do not intend to limit the scope of the invention, which is defined by the attached claims.

Example 1: Preparation of Mucoadhesive Tablets of Clonidine Hydrochloride

1A—Tablet Containing 0.1 mg Clonidine
0.1 mg (base equivalent) of clonidine hydrochloride was blended with 13 mg of dibasic calcium phosphate, 15 mg of microcrystalline cellulose, 40 mg of hydroxypropyl methyl cellulose, 1 mg of colloidal silica and 0.9 mg of magnesium stearate.

The mixture was then homogenized by sieving and 30 mg of milk protein concentrate was added and mixed with the initial mixture. The resulting composition was then compressed under sufficient pressure to form a tablet.

1B—Tablets Containing 0.05 and 0.1 mg Clonidine

An aqueous solution of clonidine hydrochloride was sprayed on a mixture composed of microcrystalline cellulose, milk protein concentrate and povidone. Granulation continued until enough cohesion of the powders was obtained. After drying and sieving, hydroxypropyl methyl cellulose was added to the granules and mixed until blend uniformity was obtained. Finally, magnesium stearate was added and mixed with the final blend. The resulting composition was then compressed under sufficient pressure to form a tablet.

1C—Tablets Containing 0.05 and 0.1 mg Clonidine

An aqueous solution of clonidine hydrochloride was sprayed on a mixture composed of microcrystalline cellulose and povidone. Granulation continued until enough cohesion of the powders was obtained. After drying and sieving, hydroxypropyl methyl cellulose, colloidal silica, talc and milk protein concentrate were added to the granules and mixed until blend uniformity was obtained. Finally, magnesium stearate was added and mixed with the final blend. The resulting composition was then compressed under sufficient pressure to form a tablet.

1D—Tablets Containing 0.05 mg Clonidine

An aqueous solution of clonidine hydrochloride was mixed with povidone. Microcrystalline cellulose and a milk protein concentrate were then added to this mixture and the resulting blend was granulated, dried and sieved. Hypromellose and colloidal silicon dioxide were then added to this powder in order to obtain a final blend to which magnesium stearate was added as a lubricant. The resulting composition was then compressed under sufficient pressure to form a tablet.

Example 2: Preventive Treatment of Skin Injury

A phase II, multicentre, randomised, double-blind, placebo-controlled study was performed to compare the efficacy of mucoadhesive buccal tablets comprising 50 µg of clonidine hydrochloride applied once daily to that of placebo in the prevention and treatment of skin injury following radiotherapy in patients with head and neck cancer (suffering from a newly diagnosed squamous cell carcinoma of the oral cavity, oropharynx, hypopharynx or larynx). These patients received, within 15 weeks after curative surgery, a cumulative radiation dose of radiation ranging from 50 to 70 Gray in oral cavity, based on a daily dosing between 1.8 and 2.2 Gy, combined with platinum-based chemotherapy, based on a weekly or tri-weekly cycle. Clonidine was administered in the form of a mucoadhesive tablet that was applied into the mouth, on the upper gum, for about 30 seconds, after which it remained in place for several hours. The treatment with clonidine hydrochloride started from 1 to 3 days before radiotherapy until the end of radiotherapy, for up to 8 weeks. Patients were evaluated twice a week during the radiotherapy period, then one month after stop of radiotherapy.

38.7% of the patients of the placebo group, but only 25.5% of the patients of treated group, showed skin injury after treatment.

This example demonstrates that Clonidine and/or Clonidine derivatives efficiently decrease the occurrence of skin adverse events due to radiotherapy.

The invention claimed is:

1. A method for reducing the risk of radiodermatitis in a subject undergoing radiotherapy, comprising
   administering by transmucosal route an effective amount of a clonidine and/or clonidine derivative selected from the group consisting of: clonidine, p-aminoclonidine, p-diethylamino clonidine, p-ethylamino clonidine, p-acetamido clonidine, p-bromoacetamido clonidine, p-N-chloroethyl-N-methylamino clonidine, p-N-β-chloroethyl-N-methylaminomethyl clonidine, 3,5-dichloro-4-(imidazolidin-2-ylideneamino)benzyl alcohol, 3,5-dichloro-4-(I,3-diisobutyryl imidazolidin-2-ylideneamino)benzyl isobutyrate, ethyl 3,5-dichloro-4-(I-isobutyrylimidazolidin-2-ylideneamino)benzoate, and mixtures thereof, to the subject,
   wherein the clonidine or clonidine derivative is administered on a daily basis 1 to 8 days before the subject begins the radiotherapy.

2. The method according to claim 1, wherein the clonidine and/or clonidine derivative comprises clonidine or a pharmaceutically acceptable salt thereof.

3. The method according to claim 1, wherein the administration provides for sustained release of the clonidine derivative.

4. The method according to claim 1, wherein the clonidine and/or clonidine derivative is in the form of a mucoadhesive tablet.

5. The method according to claim 1, wherein the clonidine and/or clonidine derivative is administered on a daily basis with a daily oral intake of clonidine or clonidine derivative ranging from 20 to 150 µg.

6. The method of claim 5, wherein pharmaceutically acceptable salt is clonidine hydrochloride.

7. The method of claim 5, wherein the clonidine and/or clonidine derivative is administered on a daily basis with a daily oral intake of clonidine or clonidine derivative ranging from 50 to 100 µg.

8. The method of claim 1, wherein the clonidine and/or clonidine derivative is administered on a daily basis from 1 to 3 days before radiotherapy until the end of the radiotherapy.

* * * * *